(12) United States Patent
Hamada et al.

(10) Patent No.: US 8,749,776 B2
(45) Date of Patent: Jun. 10, 2014

(54) APPARATUS AND METHOD FOR INSPECTING CLOTH PIECE

(75) Inventors: Kazushi Hamada, Takamatsu (JP); Yasuhiko Enami, Takamatsu (JP)

(73) Assignee: Purex Co., Ltd., Takamatsu Kagawa (JP)

( * ) Notice: Subject to any disclaimer, the term of this patent is extended or adjusted under 35 U.S.C. 154(b) by 0 days.

(21) Appl. No.: 13/496,672

(22) PCT Filed: May 17, 2011

(86) PCT No.: PCT/JP2011/002722
§ 371 (c)(1),
(2), (4) Date: Mar. 16, 2012

(87) PCT Pub. No.: WO2011/145327
PCT Pub. Date: Nov. 24, 2011

(65) Prior Publication Data
US 2013/0077093 A1    Mar. 28, 2013

(30) Foreign Application Priority Data

May 20, 2010  (JP) ................................ 2010-116428

(51) Int. Cl.
*G01N 21/00* (2006.01)
*G01N 21/898* (2006.01)
(52) U.S. Cl.
CPC .......... *G01N 21/898* (2013.01); *G01N 21/8983* (2013.01)
USPC ..................................... 356/238.3; 356/238.1
(58) Field of Classification Search
CPC .......................... G01N 21/898; G01N 21/8983
USPC ..................... 356/237.1–237.6, 238.1–238.3, 356/239.3–239.7, 429–431; 26/70; 348/88; 382/141
See application file for complete search history.

(56) References Cited

U.S. PATENT DOCUMENTS

| | | |
|---|---|---|
| 4,853,776 A | 8/1989 | Itaya et al. |
| 2005/0288850 A1 | 12/2005 | Sato |
| 2007/0073468 A1 | 3/2007 | Tsukamoto |

FOREIGN PATENT DOCUMENTS

| | | |
|---|---|---|
| JP | 63-249768 | 10/1988 |
| JP | 2001-289110 | 10/2001 |
| JP | 2010-048745 | 3/2010 |
| KR | 1020060098818 | 9/2006 |

OTHER PUBLICATIONS

EP patent application No. 12000183.9, Partial EP Search Report mailed Jun. 6, 2012.
KR patent application No. 10-2012-7003271, Office Action mailed Apr. 25, 2013.

*Primary Examiner* — Tri T Ton
(74) *Attorney, Agent, or Firm* — Weaver Austin Villeneuve & Sampson LLP (57) ABSTRACT

Provided is an apparatus and a method for inspecting a cloth piece, by which dirt and a tear can be reliably distinguished. The apparatus for inspecting a cloth piece includes: a first inspection camera 41 for picking up an image of reflected light from a cloth piece T passing through the dark color section 21; and a second inspection camera 42 for picking up an image of transmitted light through the cloth piece T passing through the transparent section 22. The dirt and the tear can be reliably distinguished by determining an area where the reflected light and transmitted light are both darker than a surrounding area to be dirt and by determining an area where the reflected light is darker than the surrounding area and the transmitted light is brighter than the surrounding area to be the tear.

6 Claims, 7 Drawing Sheets

APPARATUS AND METHOD FOR INSPECTING CLOTH PIECE

This application is a continuation of International Application No. PCT/JP2011/002722, filed May 17, 2011, priority being claimed on Japanese Patent Applications 2010-116428 filed May 20, 2010.

TECHNICAL FIELD

The present invention relates to an apparatus and a method for inspecting a cloth piece, and more particularly, to an apparatus and a method for inspecting a cloth piece, by which a cloth piece such as a towel having already been washed and dried is inspected whether or not it has an imperfection such as dirt or a tear.

BACKGROUND ART

A large number of cloth pieces such as towels are used in hotels, hospitals, and the like. Generally, those used cloth pieces are washed and dried at laundry plants for being reused in hotels, hospitals, and the like.

Cloth pieces are washed and dried at laundry plants, followed by an inspection for an imperfection such as dirt or a tear. Only cloth pieces without an imperfection are then folded by a folding machine.

In the case of a visual inspection of cloth pieces by a worker, determination of the quality may vary depending on a worker. Therefore, recently, an apparatus for inspecting a cloth piece performs this operation.

As an example of an apparatus for inspecting a cloth piece, Patent Literature 1 discloses an apparatus.

Figure 7:
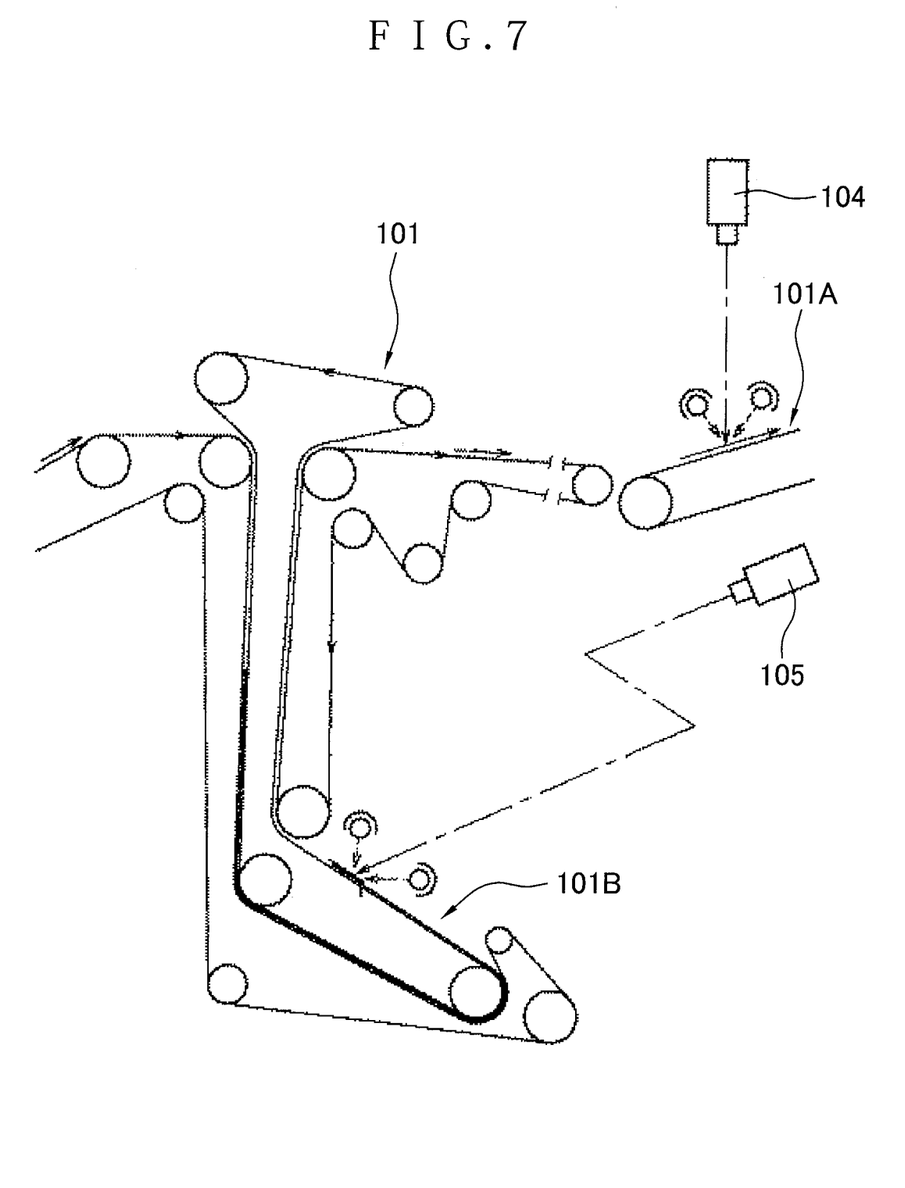
FIG. 7 is a side view of a conventional apparatus for inspecting a cloth piece.

As shown in FIG. 7, the apparatus includes a series of conveying conveyers 101, and a camera 104 for inspecting a front face of a cloth piece conveyed through a conveying part 101A for a front-facing cloth piece and a camera 105 for inspecting a back face of the cloth piece conveyed through a conveying part 101B for a back-facing cloth piece in the series of the conveying conveyers 101.

A cloth piece is conveyed to the conveying part 101A for a front-facing cloth piece and the conveying part 101B for a back-facing cloth piece, and the cameras 104 and 105 pick up images thereof. This enables an inspection of the both front and back faces.

According to a result of the inspection, a cloth piece having dirt is subjected to rewashing, while a cloth piece having a tear is discarded. However, the cloth piece having a tear may be subjected to rewashing because a conventional apparatus for inspecting a cloth piece has difficulty in distinguishing between dirt and a tear. The cloth piece having a tear is to be washed for many times in the case. Improvement in processing efficiency has been therefore desired by reliably distinguishing between dirt and a tear and discarding a cloth piece having a tear.

In the case where pile fabric of a towel does not have dirt but a ground thereof has dirt, it is difficult to detect the dirt. Improvement of accuracy in detecting such dirt therefore has been desired, as well.

CITATION LIST

Patent Literature

Patent Literature 1: Japanese Patent Laid-Open No. 2004-177143

SUMMARY OF INVENTION

Technical Problem

In view of the above circumstances, an object of the present invention is to provide an apparatus and a method for inspecting a cloth piece, by which dirt and a tear can be reliably distinguished, and which have high accuracy to detect the dirt.

Solution to Problem

An apparatus for inspecting a cloth piece according to a first feature of the present invention includes: an inspection table through which a cloth piece passes, the inspection table having a dark color section and a light transmitting section; a first inspection camera for picking up an image of reflected light from a cloth piece passing through the dark color section; and a second inspection camera for picking up an image of transmitted light through a cloth piece passing through the light transmitting section.

An apparatus for inspecting a cloth piece according to a second feature of the present invention is the first feature of the present invention, further including: a first conveyor to which the cloth piece is supplied; and a second conveyor connected to the first conveyor, wherein the inspection table is arranged between the first conveyor and the second conveyor, an edge of the inspection table at a side of the second conveyor is arranged to protrude from a connection line between a rear end of the first conveyor and a front end of the second conveyor, and a velocity of the second conveyor is faster than that of the first conveyor.

A method for inspecting a cloth piece according to a fifth feature of the present invention includes the steps of: picking up an image of reflected light from a cloth piece; picking up an image of transmitted light through the cloth piece; determining an area where the reflected light and the transmitted light are both darker than a surrounding area to be dirt at the same position of the cloth piece; and determining an area where the reflected light is darker than the surrounding area and the transmitted light is brighter than the surrounding area to be a tear at the same position of the cloth piece.

Advantageous Effects of Invention

According to the first feature of the present invention, the first inspection camera picks up an image of the reflected light from the cloth piece passing through the dark color section. Therefore, an image of the dirt on the cloth piece can be picked up darker than that of the surrounding area, as well as an image of the tear can be picked up darker than that of the surrounding area as a color of the dark color section. Also, the second inspection camera picks up an image of the transmitted light through the cloth piece passing through the light transmitting section. Therefore, an image of the tear can be picked up brighter than that of the surrounding area, as well as dirt inside the cloth piece which cannot be detected by the reflected light is emphasized to be able to pick up an image thereof darker than that of the surrounding area. Accordingly, dirt and a tear can be reliably distinguished by determining an area where the reflected light and the transmitted light are both darker than a surrounding area to be dirt at the same position of the cloth piece, and by determining an area where the reflected light is darker than the surrounding area and the transmitted light is brighter than the surrounding area to be a tear at the same position of the cloth piece. Therefore, a cloth piece having dirt can be subjected to rewashing, while a cloth piece having a tear can be discarded, leading to avoid washing the cloth piece having a tear for many times and achieving excellent processing efficiency. Since an image of the transmitted light is also picked up, dirt inside the cloth piece which cannot be detected by the reflected light is emphasized, providing high accuracy to detect the dirt.

According to the second feature of the present invention, the velocity of the second conveyor is faster than that of the first conveyor, thereby applying a force to pull to the cloth piece in a longitudinal direction. This enables to smooth out a crease in the cloth piece. Since the inspection table is arranged to protrude, the cloth piece rubs against the inspection table when passing between the first conveyor and the second conveyor. The cloth piece rubs against the inspection table while being pulled by the first conveyor and the second conveyor, thereby allowing the crease in the cloth piece to be smoothed out. Accordingly, smoothing out a crease in the cloth piece and imperfection inspection can be simultaneously carried out, thereby providing a small apparatus as a whole and achieving a fast processing speed.

According to the third feature of the present invention, dirt and a tear can be reliably distinguished by determining an area where the reflected light and the transmitted light are both darker than a surrounding area to be dirt at the same position of the cloth piece, and by determining an area where the reflected light is darker than the surrounding area and the transmitted light is brighter than the surrounding area to be a tear at the same position of the cloth piece. Therefore, a cloth piece having dirt can be subjected to rewashing, while a cloth piece having a tear can be discarded, leading to avoid washing the cloth piece having a tear for many times and achieving excellent processing efficiency.

DESCRIPTION OF EMBODIMENTS

Next, an embodiment of the present invention will be described with reference to the drawings.

First Embodiment

Figure 1:
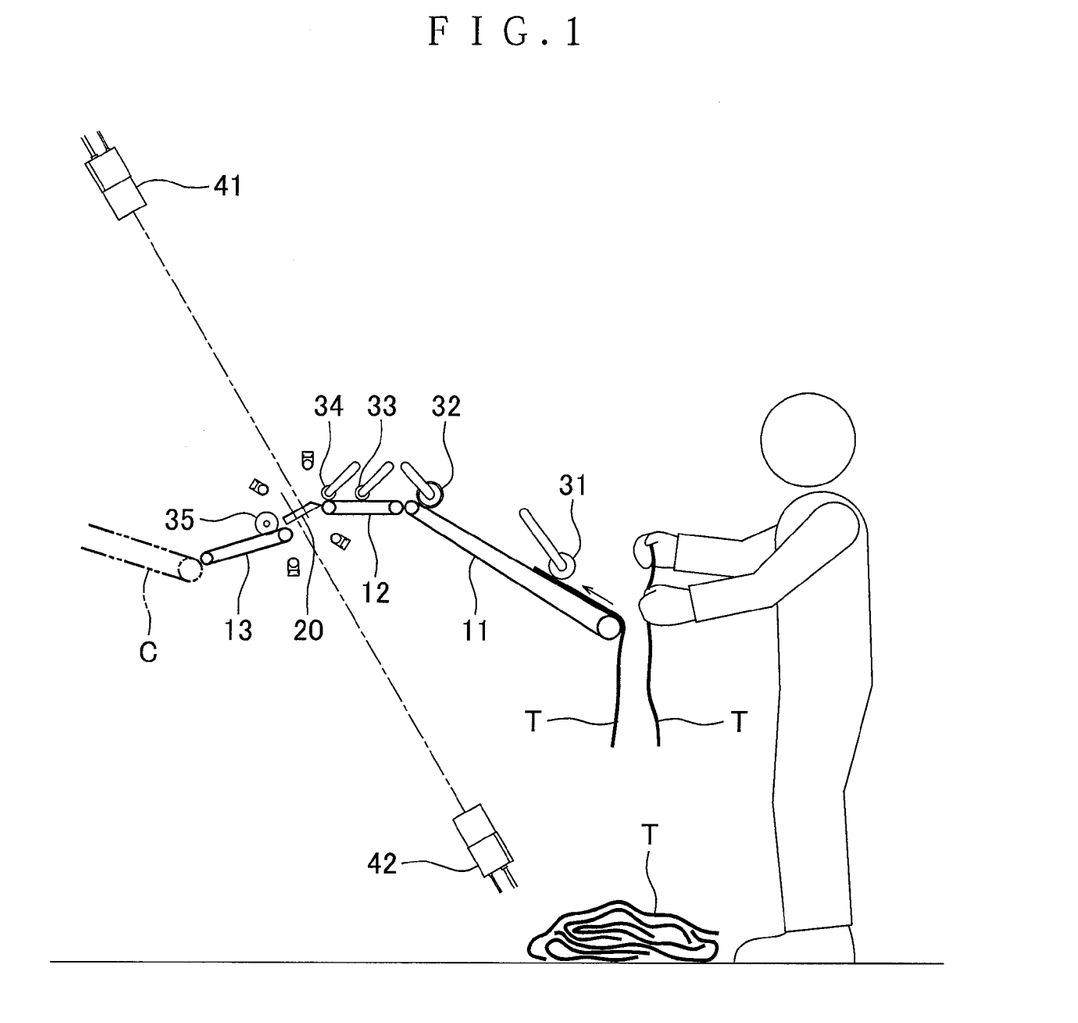
FIG. 1 is a side view of an apparatus for inspecting a cloth piece according to a first embodiment of the present invention.

As show in FIG. 1, an apparatus for inspecting a cloth piece according to a first embodiment of the present invention is integrated with an apparatus for smoothing out a crease in a cloth piece, and includes a first conveyor 11, a second conveyor 12 and a third conveyor 13, each of which is fixed by a not-shown frame.

The first conveyor 11 is a conveyor on which a worker put a cloth piece T such as a washed and dried towel. A front end (a right end in FIG. 1) of the conveyor 11 is approximately as high as a waist of the worker so that the worker easily puts the cloth piece T thereon. An inclination of the first conveyor 11 causes a put-on face to face the worker. The second conveyor 12 is connected to a rear end (left end in FIG. 1) of the first conveyor 11, while the third conveyor 13 is connected to a rear end of the second conveyor 12. An apparatus for a subsequent process, for example, a conveyor C of a folding apparatus is then connected to a rear end of the third conveyor 13.

A width of the first, second and third conveyors 11, 12 and 13 is adapted to be wide enough for a width of the cloth piece T to fit on.

A velocity of the second conveyor 12 is faster than that of the first conveyor 11, while a velocity of the third conveyor 13 is faster than that of the second conveyor 12. For example, the velocities of the first conveyor 11, the second conveyor 12 and the third conveyor 13 are set to be 15 m/min, 25 to 30 m/min and 50 m/min, respectively.

An inspection table 20 is fixed between the rear end of the second conveyor 12 and a front end of the third conveyor 13. The inspection table 20 is a rectangular plate in plan view having the same width as the first, second and third conveyors 11, 12 and 13. A front edge (an edge at a side of the second conveyor 12) of the inspection table 20 is approximately as high as the rear end of the second conveyor 12 or slightly lower. The cloth piece T is adapted to smoothly pass from the second conveyor 12 to the inspection table 20. A rear edge (an edge at a side of the third conveyor 13) of the inspection table 20 is set to be higher than the front end of the third conveyor 13. That is, the rear edge of the inspection table 20 is arranged to protrude from a connection line between the rear end of the second conveyor 12 and the front end of the third conveyor 13.

Pressure rollers 31 to 35 are provided above the first, second and third conveyors 11, 12 and 13 for pressing the cloth piece T against put-on faces of the conveyors 11, 12 and 13. The first pressure roller 31 is arranged at the front (right side in FIG. 1) of the first conveyor 11 for pressing the cloth piece T put on by the worker so as not to fall down. The second pressure roller 32 is arranged at the rear end of the first conveyor 11, while the third pressure roller 33 is arranged around the middle of the second conveyor 12. Each of the second and third pressure rollers 32 and 33 presses the cloth piece T so that the cloth piece T moves according to the velocities of the first conveyor 11 and the second conveyor 12. The fourth pressure roller 34 is arranged at the rear end of the second conveyor 12, while the fifth pressure roller 35 is arranged at the front end of the third conveyor 13. Each of the fourth and fifth pressure rollers 34 and 35 presses the cloth piece T so that the cloth piece T moves according to the velocities of the second conveyor 12 and the third conveyor 13 as well as that the cloth piece T rubs against the inspection table 20.

Note that a first conveyor and a second conveyor set forth in Claims are conveniently numbered and another conveyor may be further provided at a front or a rear thereof. The second conveyor 12 corresponds to the first conveyor set forth in Claims, while the third conveyor 13 corresponds to the second conveyor set forth in Claims in the present embodiment.

Additionally, in an embodiment, another pressure mechanism may be provided instead of the pressure rollers 31 to 35. For example, a vacuum box may be provided below the conveyors 11, 12 and 13, or a pressure conveyor may be provided so as to face the put-on faces of the conveyors 11, 12 and 13 and to come in contact therewith.

According to the above configuration, an operation of the first conveyor 11 causes the cloth piece T to move in an arrow direction in FIG. 1 when the worker picks out and laterally stretches one side of the washed and dried cloth piece T to put the side thereof on the first conveyor 11. When a front part of the cloth piece T moves over the second conveyor 12, a difference between the velocities of the first and second conveyors 11 and 12 causes a force to pull to be applied to the cloth piece T in a longitudinal direction (a lateral direction in FIG. 1), thereby enabling to smooth out a crease in the cloth piece T. Further, when the front part of the cloth piece T passes over the inspection table 20 to move over the third conveyor 13, a difference between the velocities of the second and third conveyors 12 and 13 causes the force to pull to be applied to the cloth piece T in the longitudinal direction. The cloth piece T is moreover stretched from the rear edge of the inspection table 20 toward the fifth pressure roller 35 in a slanting downward direction, so that the cloth piece T rubs against the rear edge of the inspection table 20. This enables to smooth out the crease in the cloth piece 20 completely.

As described above, smoothing out a crease in the cloth piece and imperfection inspection described later can be simultaneously carried out, thereby providing a small apparatus as a whole and achieving a fast processing speed.

Figure 2:
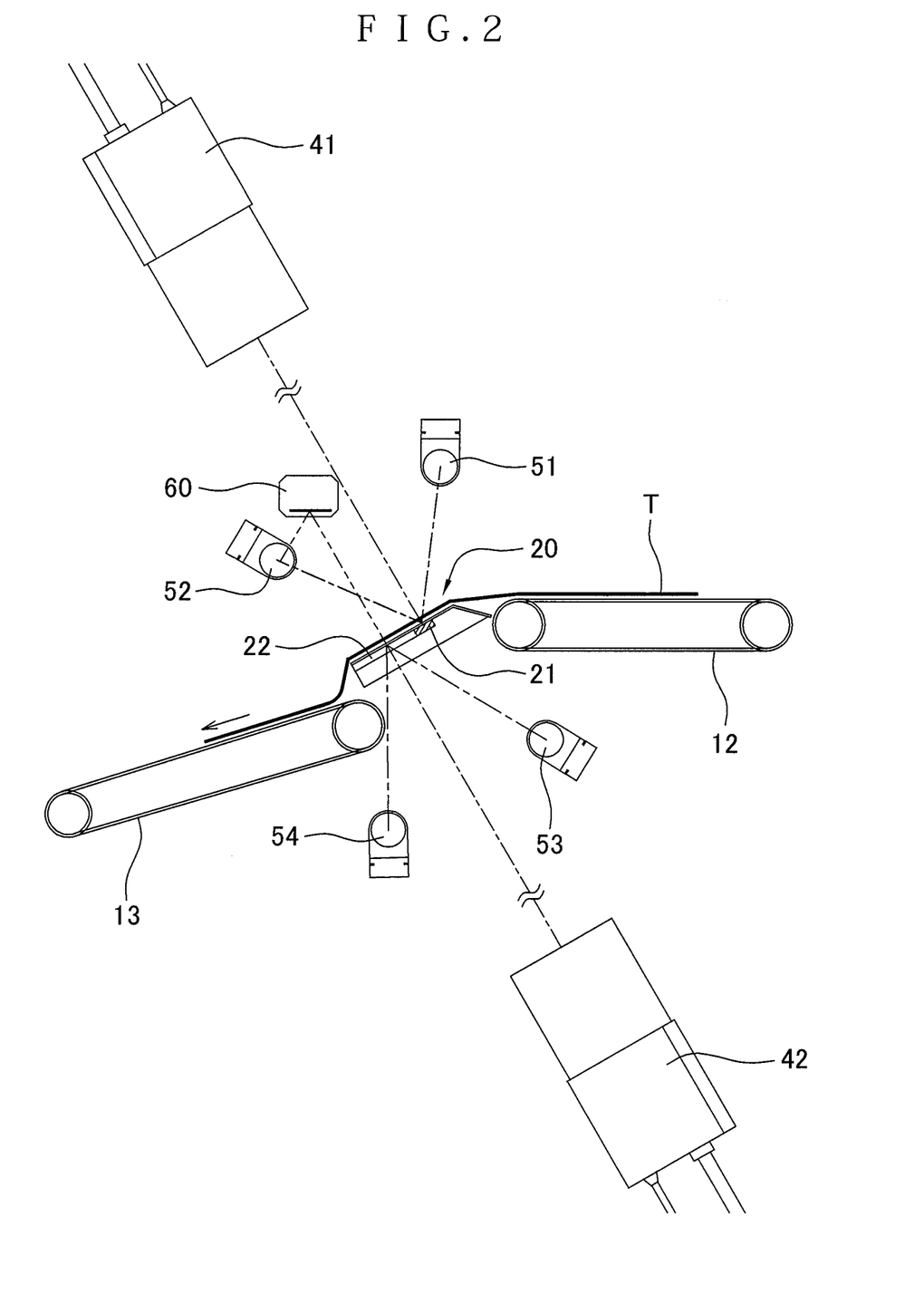
FIG. 2 is a partial enlarged side view of the apparatus for inspecting a cloth piece.

As shown in FIG. 2, a first inspection camera 41 for picking up an image of a front face of a cloth piece T passing through the inspection table 20 is provided at a front face side of the inspection table 20 (an upper side in FIG. 2). A second inspection camera 42 for picking up an image of a back face of the cloth piece T passing through the inspection table 20 is provided at a back face side of the inspection table 20 (a lower side in FIG. 2). The first and second inspection cameras 41 and 42 are connected to a not-shown image processing apparatus, thereby enabling to output a picked-up image as an electric signal.

Examples of the first and second inspection cameras 41 and 42 include a line camera for picking up an image of the cloth piece T linearly in a width direction thereof (a direction perpendicular to a paper face in FIG. 2).

For the convenience of the description, a face of the cloth piece T not in contact with the inspection table 20 is regarded as a front face, while a face thereof in contact with the inspection table 20 is regarded as a back face. The definition of these front face and back face therefore does not necessarily correspond to an actual front face and a back face of the cloth piece T. Also, a front face and a back face set forth in Claims do not necessarily correspond to the actual front face and the back face of the cloth piece.

The inspection table 20 includes a black color section 21 and a transparent section 22. The black color section 21 is formed in a belt-like shape in a width direction (the direction perpendicular to the paper face in FIG. 2) at a side of the second conveyor 12 of the inspection table 20. The transparent section 22 is formed in a belt-like shape in the width direction at a side of the third conveyor 13 of the inspection table 20.

The first inspection camera 41 picks up an image of the front face of the cloth piece T passing through the black color section 21 at an image pick-up position over the black color section 21. On the other hand, the second inspection camera 42 picks up through the transparent section 22 an image of the back face of the cloth piece T passing through the transparent section 22 at an image pick-up position over the transparent section 22.

The black color section 21 corresponds to a dark color section set forth in Claims. Another color such as gray may be applied to the black color section 21 instead of black. An optimal color may be selected for imperfection detection described later. The transparent section 22 corresponds to a light transmitting section set forth in Claims. A material allowing light to pass through such as a translucent white material may be applied to the transparent section 22 instead of a transparent material. An optimal color may also be selected for imperfection detection described later.

Four light sources 51, 52, 53 and 54 for illumination such as a fluorescent are provided around the inspection table 20. The first light source 51 and the second light source 52 are provided at the front face side of the inspection table 20 for illuminating the image pick-up position of the first inspection camera 41. The third light source 53 and the fourth light source 54 are provided at the back face side of the inspection table 20 for illuminating the image pick-up position of the second inspection camera 42. Therefore, the first inspection camera 41 can pick up an image of reflected light from the front face of the cloth piece, while the second inspection camera 42 can pick up an image of reflected light from the back face of the cloth piece.

A mirror 60 is also provided close to the second light source 52 to reflect light from the second light source 52, so that the image pick-up position of the second inspection camera 42 is illuminated from the front face side. The light from the second light source 52 therefore passes through the passing cloth piece T from the front face side to the back face side, thereby allowing an image of the transmitted light to be picked up by the second inspection camera 42.

According to the above configuration, operations of the second and third conveyors 12 and 13 cause the cloth piece T to move in an arrow direction in FIG. 2. When the cloth piece T passes over the inspection table 20, the first inspection camera 41 and the second inspection camera 42 can pick up images of reflected light from the front face of the cloth piece, and reflected light from and transmitted light through the back face of the cloth piece, respectively.

Figure 3:
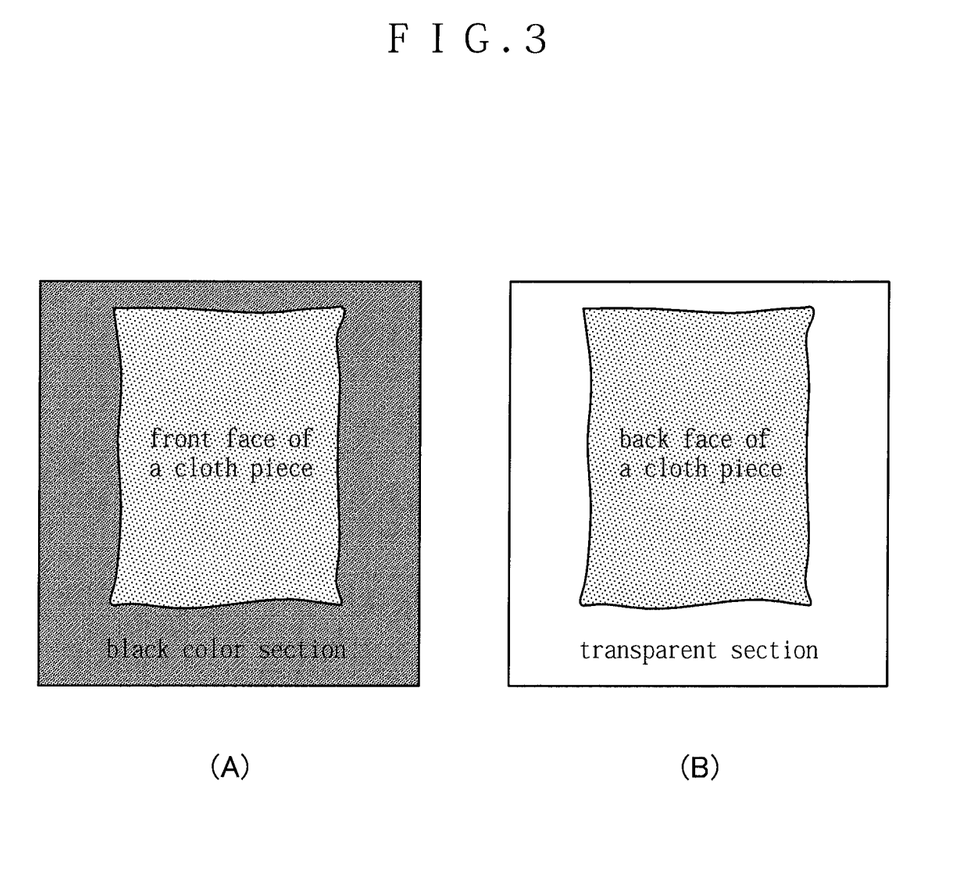
FIG. 3 shows diagrams illustrating (A) an image of a front face of a cloth piece and (B) an image of a back face of the cloth piece obtained by the apparatus for inspecting a cloth piece.

FIG. 3 shows images obtained by making images picked up by the first and second inspection cameras 41 and 42 planate by the image processing apparatus. That is, obtained are an image (A) of the front face of the cloth piece with a background black (the black color section 21), and an image (B) of the back face of the cloth piece with a background white (light passing through the transparent section 22).

Figure 4:
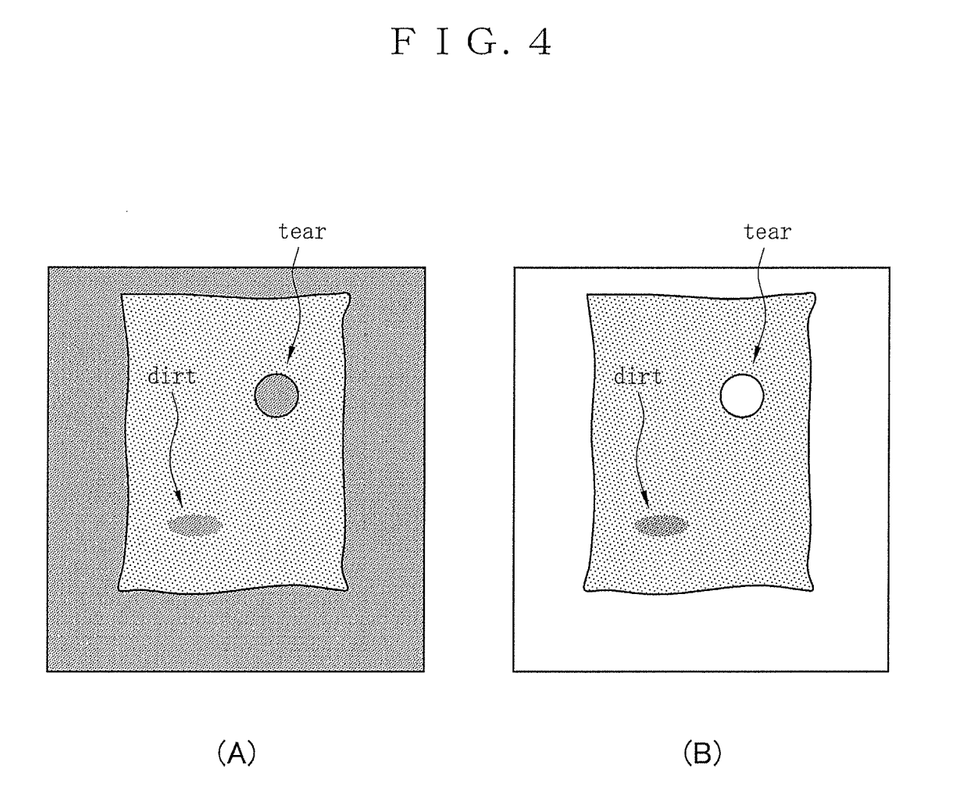
FIG. 4 shows diagrams illustrating (A) an image of a front face of a cloth piece and (B) an image of a back face of the cloth piece in the case of the cloth piece having dirt and a tear.

FIG. 4 shows obtained images in the case of the cloth piece T having dirt and a tear.

The dirt and the tear are both shown darker than a surrounding area (a color of the cloth piece) in the image (A) of the front face of the cloth piece. This is because a dirty area becomes darker by a color of the dirt itself, while a torn area becomes darker by a color of the black color section 21 viewed through a torn hole. On the other hand, the dirt is shown darker than the surrounding area and the tear is shown brighter than the surrounding area in the image (B) of the back face of the cloth piece. This is because the dirty area becomes darker by the color of the dirt itself, while the torn area becomes brighter by light directly arriving from the second light source 52 through the torn hole.

At the same position of the cloth piece T, an area darker than the surrounding area on both the front face and back face can therefore be determined to be dirt by comparing the image (A) of the front face of the cloth piece with the image (B) of the back face of the cloth piece. Also, at the same position of the cloth piece T, an area darker than the surrounding area on the front face and brighter than the surrounding area on the back face can be determined to be a tear.

By reliably distinguishing between dirt and a tear in such a manner, a cloth piece T having dirt can be subjected to rewashing, while a cloth piece T having a tear can be discarded. This leads to avoid washing the cloth piece T having a tear for many times and achieving excellent processing efficiency.

A conveyor or the like connected behind the third conveyor 13 is operated according to an inspection result derived from the image processing apparatus. This enables to automatically distinguish between a cloth piece T without an imperfection, a cloth piece T with dirt and a cloth piece T with a tear.

Figure 5:
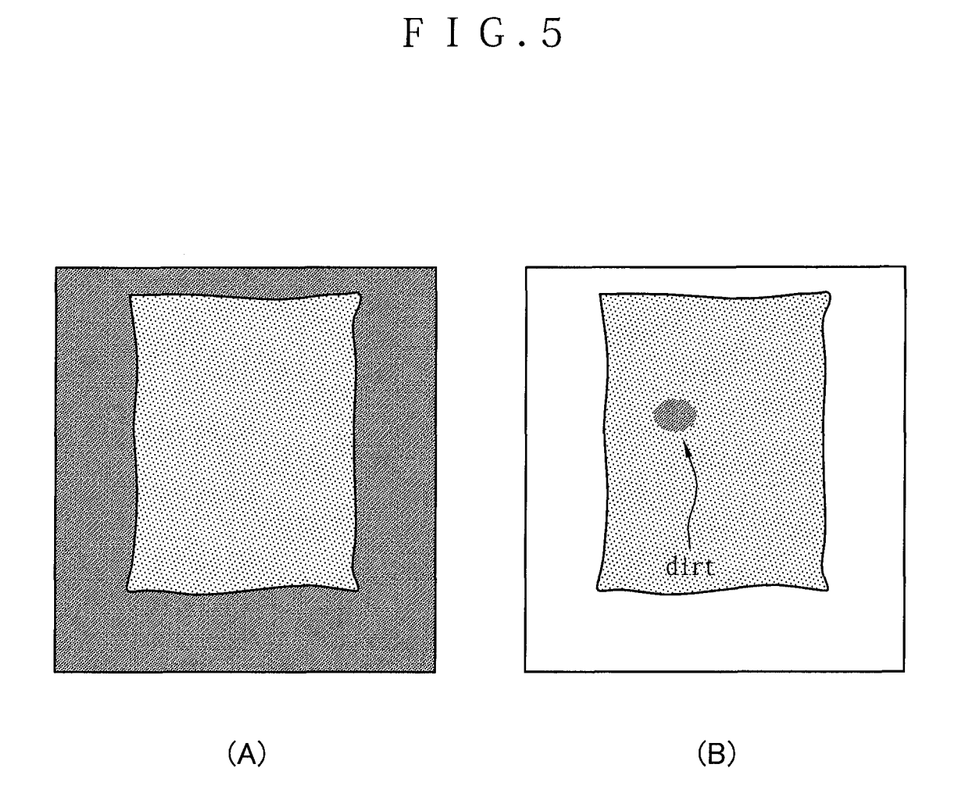
FIG. 5 shows diagrams illustrating (A) an image of a front face of a cloth piece and (B) an image of a back face of the cloth piece in the case of the cloth piece having dirt inside.

FIG. 5 shows obtained images in the case of a cloth piece T having dirt inside.

This is a case, for example, where pile fabric of a towel does not have dirt but a ground thereof has dirt. Such dirt does not appear on a surface, thereby leading to a difficulty in detecting it by picking up an image of reflected light.

As shown in FIG. 5, dirt inside the cloth piece is shown slightly darker than a surrounding area in an image (A) of a front face of the cloth piece. On the other hand, the dirt inside the cloth piece is shown darker than the surrounding area by picking up an image of transmitted light for emphasizing the dirt in an image (B) of a back face of the cloth piece.

As a result, the dirt inside the cloth piece which cannot be detected by the reflected light can be detected, providing high detection accuracy.

The first inspection camera picks up an image of the reflected light from the front face of the cloth piece, as well as the second inspection camera picks up an image of the reflected light from the back face of the cloth piece. This therefore enables detection of dirt even on one face of the cloth piece.

Specifically, at the same position of the cloth piece T, the determination of dirt can also be made on an area that is darker than a surrounding area on either a front or a back face of the cloth piece T and that is approximately as bright as the surrounding area on the other face. This enables detection of dirt even on one face of the cloth piece, providing high detection accuracy.

Further, the second inspection camera 42 can directly pick up an image of light from the second light source 52 under a normal condition (at the time of the cloth piece T not passing through the inspection table 20). This enables to monitor a level of an amount of light from the second light source 52 under the normal condition, thereby being able to make deterioration determination on the light sources 51, 52, 53 and 54.

Second Embodiment

Figure 6:
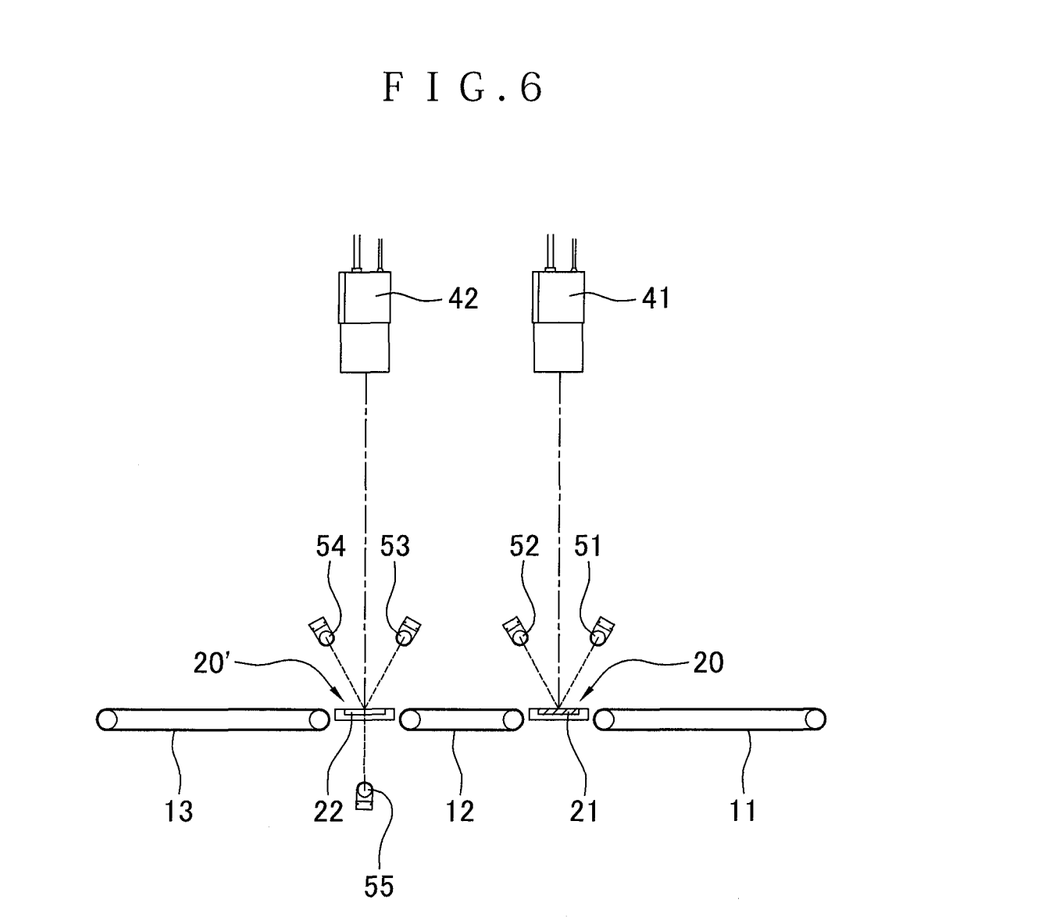
FIG. 6 is a side view of an apparatus for inspecting a cloth piece according to a second embodiment of the present invention.

As shown in FIG. 6, an apparatus for inspecting a cloth piece according to a second embodiment of the present invention is not integrated with an apparatus for smoothing out a crease in a cloth piece unlike the apparatus for inspecting a cloth piece in the first embodiment. The apparatus for inspecting a cloth piece can be apparently an individual apparatus in such a manner. Additionally, with a configuration where images of reflected light from and transmitted light through a cloth piece T can be picked up, it is possible to integrate with another apparatus other than the apparatus for smoothing out a crease in a cloth piece. Considering a size of the whole apparatus, processing efficiency or the like, an optimal arrangement of the apparatus for inspecting a cloth piece can be selected.

The apparatus for inspecting a cloth piece according to the present embodiment includes a first conveyor 11, a second conveyor 12 and a third conveyor 13, each of which is fixed by a not-shown frame. A first inspection table 20 only having a black color section 21 is fixed between a rear end of the first conveyor 11 and a front end of the second conveyor 12. A second inspection table 20' only having a transparent section 22 is fixed between a rear end of the second conveyor 12 and a front end of the third conveyor 13.

An inspection table set forth in Claims is not limited to a single element but includes a concept of a plurality of elements separated into a dark color section and a transparent section.

Another color such as gray may be applied to the black color section 21 instead of black, while a material allowing light to pass through such as a translucent white material may be applied to the transparent section 22 instead of a transparent material.

A first inspection camera 41 for picking up an image of a front face of a cloth piece T passing through the black color section 21 is provided at a front face side of the first inspection table 20. A second inspection camera 42 for picking up an image of the front face of the cloth piece T passing through the transparent section 22 is provided at a front face side of the second inspection table 20'. An image pick-up position for the first inspection camera 41 is above the black color section 21, while an image pick-up position for the second inspection camera 42 is above the transparent section 22.

First light source 51 and second light source 52 are provided at the front face side of the first inspection table 20 for illuminating the image pick-up position of the first inspection camera 41. Third light source 53 and fourth light source 54 are provided at the front face side of the second inspection table 20' for illuminating the image pick-up position of the second inspection camera 42. Therefore, the both first and second inspection cameras 41 and 42 can pick up images of reflected light from the front face of the cloth piece.

A fifth light source 55 is also provided at a back face side of the second inspection table 20' for illuminating the image pick-up position of the second inspection camera 42 from the back face side. Light from the fifth light source 55 therefore passes through the passing cloth piece T from the back face side to the front face side, thereby allowing an image of the transmitted light to be picked up by the second inspection camera 42.

According to the above configuration, operations of the first, second and third conveyors 11, 12 and 13 cause the cloth piece T to move to the left in FIG. 6. When the cloth piece T passes over the first and second inspection tables 20 and 20', the first inspection camera 41 and the second inspection camera 42 can pick up images of reflected light from the front face of the cloth piece, and reflected light from and transmitted light through the front face of the cloth piece, respectively.

According to the present embodiment, similarly to the first embodiment, dirt and a tear are both shown darker than a surrounding area in the image picked up by the first inspection camera 41. On the other hand, the dirt is shown darker than the surrounding area and the tear is shown brighter than the surrounding area in the image picked up by the second inspection camera 42. Therefore, the dirt and the tear can be reliably distinguished, providing high processing efficiency.

In the image picked up by the second inspection camera 42, dirt inside the cloth piece is shown darker than the surrounding area by picking up an image of transmitted light for emphasizing the dirt. As a result, the dirt inside the cloth piece which cannot be detected by the reflected light can be detected, providing high detection accuracy.

Further, the second inspection camera 42 can monitor a level of an amount of light from the fifth light source 55 under a normal condition, thereby being able to make deterioration determination on the light sources 51, 52, 53 and 54.

Since the second inspection camera 42 is provided at the front face side of the second inspection table 20', an image of reflected light from the back face of the cloth piece cannot be picked up. However, even dirt only on a back face of a cloth piece can be shown darker than the surrounding area by transmitted light, thereby enabling detection.

As described above, the inspection table 20 is not necessarily limited to one. It may be provided by dividing into two of a black color section 21 and a transmitted section 22. Additionally, the second inspection camera 42 is not necessarily provided the back face side of the inspection table 20 and it may be provided at the front face side. An optimal arrangement may be selected under constraints such as a size, a shape and the like of the apparatus for inspecting a cloth piece.

REFERENCE SIGNS LIST

11, 12, 13 conveyor
20 inspection table
21 black color section
22 transparent section
41 first inspection camera
42 second inspection camera
51, 52, 53, 54, 55 light source
60 mirror

The invention claimed is:

1. An apparatus for inspecting a cloth piece, comprising:
   an inspection table through which a cloth piece passes, the inspection table having a dark color section and a light transmitting section;
   a first inspection camera for picking up an image of reflected light from a cloth piece passing through the dark color section; and
   a second inspection camera for picking up an image of transmitted light through a cloth piece passing through the light transmitting section.

2. The apparatus for inspecting a cloth piece according to claim 1, further comprising:
   a first conveyor to which the cloth piece is supplied; and
   a second conveyor connected to the first conveyor, wherein
   the inspection table is arranged between the first conveyor and the second conveyor,
   an edge of the inspection table at a side of the second conveyor is arranged to protrude from a connection line between a rear end of the first conveyor and a front end of the second conveyor, and
   a velocity of the second conveyor is faster than that of the first conveyor.

3. A method for inspecting a cloth piece, comprising the steps of:
   causing a cloth piece to pass through an inspection table having a dark color section and a light transmitting section;
   picking up an image of reflected light from the cloth piece that passes through the dark color section;
   picking up an image of transmitted light through the cloth piece that passes through the light transmitting section;
   determining an area where the reflected light and the transmitted light are both darker than a surrounding area to be dirt at the same position of the cloth piece; and
   determining an area where the reflected light is darker than the surrounding area and the transmitted light is brighter than the surrounding area to be a tear at the same position of the cloth piece.

4. A method for inspecting a cloth piece, comprising the steps of:
   causing a cloth piece to pass through an inspection table having a dark color section and a light transmitting section;
   picking up an image of reflected light from the cloth piece that passes through the dark color section;
   picking up an image of transmitted light through the cloth piece that passes through the light transmitting section; and
   distinguishing between dirt and a tear by determining an area where the reflected light and the transmitted light are both darker than a surrounding area to be dirt at the same position of the cloth piece, and by determining an area where the reflected light is darker than the surrounding area and the transmitted light is brighter than the surrounding area to be a tear at the same position of the cloth piece.

5. The apparatus for inspecting a cloth piece according to claim 1, further comprising:
   an image processing apparatus connected to the first inspection camera and the second inspection camera, wherein
   the image processing apparatus determines an area where the reflected light and the transmitted light are both darker than a surrounding area to be dirt at the same position of the cloth piece, and determines an area where the reflected light is darker than the surrounding area and the transmitted light is brighter than the surrounding area to be a tear at the same position of the cloth piece.

6. The apparatus for inspecting a cloth piece according to claim 1, further comprising:
   an image processing apparatus connected to the first inspection camera and the second inspection camera, wherein
   the image processing apparatus distinguishes between dirt and a tear by determining an area where the reflected light and the transmitted light are both darker than a surrounding area to be dirt at the same position of the cloth piece, and by determining an area where the reflected light is darker than the surrounding area and the transmitted light is brighter than the surrounding area to be a tear at the same position of the cloth piece.

* * * * *